United States Patent
Minamino et al.

(10) Patent No.: US 9,095,600 B2
(45) Date of Patent: Aug. 4, 2015

(54) PROPHYLACTIC AND/OR THERAPEUTIC AGENT FOR CARDIAC INFARCTION

(75) Inventors: Tetsuo Minamino, Suita (JP);
Masafumi Kitakaze, Suita (JP);
Masatsugu Hori, Suita (JP); Hiroyuki Takahama, Suita (JP); Hiroshi Kikuchi, Edogawa-ku (JP); Kouichi Hashimoto, Edogawa-ku (JP); Hideo Kobayashi, Edogawa-ku (JP); Ayako Iijima, Edogawa-ku (JP); Daigo Asano, Edogawa-ku (JP)

(73) Assignees: OSAKA UNIVERSITY, Suita-shi (JP); NATIONAL CEREBRAL AND CARDIOVASCULAR CENTER, Osaka (JP); DAIICHI SANKYO COMPANY, LIMITED, Tokyo (JP)

(*) Notice: Subject to any disclaimer, the term of this patent is extended or adjusted under 35 U.S.C. 154(b) by 973 days.

(21) Appl. No.: 12/562,887

(22) Filed: Sep. 18, 2009

(65) Prior Publication Data
US 2010/0098753 A1  Apr. 22, 2010

Related U.S. Application Data

(63) Continuation of application No. PCT/JP2008/000652, filed on Mar. 19, 2008.

(30) Foreign Application Priority Data

Mar. 20, 2007  (JP) .................................. 2007-073016

(51) Int. Cl.
*A61K 9/127* (2006.01)
*A61K 31/7076* (2006.01)

(52) U.S. Cl.
CPC ............. *A61K 31/7076* (2013.01); *A61K 9/127* (2013.01)

(58) Field of Classification Search
CPC ... A61K 9/127; A61K 9/1271; A61K 9/1272; A61K 9/1273
USPC .......................................................... 424/450
See application file for complete search history.

(56) References Cited

U.S. PATENT DOCUMENTS 4,789,734 A * 12/1988 Pierschbacher ............... 530/395
5,527,538 A *  6/1996 Baldeschwieler ........... 424/1.21
(Continued)

FOREIGN PATENT DOCUMENTS

EP    0 526 866 A1   2/1993
JP    5208993 A      8/1993
(Continued)

OTHER PUBLICATIONS

Masatsugu Hori, et al., "Beneficial Role of Adenosine in Myocardial Ischemic and Reperfusion Injury", Drug Development Research, vol. 28, 1993, pp. 432-437.

(Continued)

*Primary Examiner* — Gollamudi Kishore
(74) *Attorney, Agent, or Firm* — Oblon, McClelland, Maier & Neustadt, L.L.P.

(57) ABSTRACT

The present invention relates to a novel preventive and/or therapeutic drug for myocardial infarction.
The present invention provides a preventive and/or therapeutic drug for myocardial infarction or myocardial ischemia-reperfusion injury, the drug containing a lipid membrane structure retaining adenosine.

17 Claims, 5 Drawing Sheets

(56) References Cited

U.S. PATENT DOCUMENTS

| | | | |
|---|---|---|---|
| 5,843,473 A * | 12/1998 | Woodle et al. | 424/450 |
| 5,852,000 A | 12/1998 | Ichihara et al. | |
| 6,440,947 B1 * | 8/2002 | Barron et al. | 514/46 |
| 6,599,283 B1 * | 7/2003 | Marzilli et al. | 604/509 |
| 6,623,671 B2 * | 9/2003 | Coe et al. | 264/4.3 |
| 6,627,732 B1 * | 9/2003 | Sakon et al. | 530/331 |
| 6,726,925 B1 * | 4/2004 | Needham | 424/450 |
| 2002/0151508 A1 * | 10/2002 | Emanuel et al. | 514/34 |
| 2004/0142014 A1 | 7/2004 | Litvack et al. | |
| 2006/0205671 A1 * | 9/2006 | Vinten-Johansen | 514/18 |
| 2007/0082042 A1 * | 4/2007 | Park et al. | 424/450 |

FOREIGN PATENT DOCUMENTS

| | | |
|---|---|---|
| JP | 2003-506310 | 2/2003 |
| JP | 2003-506310 A | 2/2003 |
| JP | 2006505365 | 2/2006 |
| WO | WO 95/05832 | 3/1995 |
| WO | WO 99/17784 A1 | 4/1999 |

OTHER PUBLICATIONS

Allan M. Ross, et al., "A Randomized, Double-Blinded, Placebo-Controlled Multicenter Trial of Adenosine as an Adjunct to Reperfusion in the Treatment of Acute Myocardial Infarction (AMISTAD-II)", Journal of the American College of Cardiology, vol. 45, No. 11, 2005, pp. 1775-1780.

JAPIC Iroyo-yo Iyakuhin-shu (Data on Drugs for Medical Use), edited and published by Japan Pharmaceutical Information Center, Sep. 1, 2006, pp. 88-90, (with partial English translation).

Office Action issued on Apr. 9, 2013 in corresponding Japanese Patent Application No. 2009-505085 (with partial English translation) 7 pp.

Forman, M. B. et al., Role of adenosine as adjunctive therapy in acute myocardial infarction, Cardiovasc Drug Rev. 2006, vol. 24, No. 2, pp. 116-147.

Verma, D. D. et al., ATP-loaded liposomes effectively protect mechanical functions of the myocardium from global ischemia in an isolated rat heart model, J Control Release, 2005, vol. 108, No. 2-3, pp. 460-471.

Brailoiu, E. et al., Effects of liposomeentrapped adenosine in the isolated rat aorta, Eur J Pharmacol, 1993, vol. 250, No. 3, pp. 489-492.

Office Action mailed Apr. 9, 2014 in corresponding Japanese patent application No. 2009-505085 with English translation, 7 pp.

Response to the Japanese Office Action mailed Apr. 9, 2014 with English translation, 9 pp.

ADENOSCAN®, (adenosine injection) for Intravenous Infusion Only, (with Japanese Version), 12 pp.

Peter Ferdinandy, et al., Pharmacological Reviews, vol. 59, No. 4, pp. 418-458, 2007, Interaction of Cardiovascular Risk Factors with Myocardial Ischemia/Reperfusion Injury, Preconditioning, and Postconditioning.

Mervyn B. Forman, et al. Cardiovascular Drug Reviews, vol. 24, No. 2, pp. 116-147, 2006, "Role of Adenosine as Adjunctive Therapy in Acute Myocardial Infarction".

D.D. Verma, et al., Journal of Controlled Release 108 (2005) 460-471, www.sciencedirect.com, "ATP-loaded liposomes effectively protect mechanical functions of the myocardium from global ischemia in an isolated rat heart model".

* cited by examiner

* : p<0.05 v.s. Control group

PROPHYLACTIC AND/OR THERAPEUTIC AGENT FOR CARDIAC INFARCTION

TECHNICAL FIELD

The present invention relates to a novel preventive and/or therapeutic drug for myocardial infarction.

BACKGROUND ART

In Japan, about 40,000 people are thought to die of acute myocardial infarction each year. In the United States, it is estimated that about 1.5 million people develop myocardial infarction every year, and among them, the number of deaths is about 600,000. Acute myocardial infarction is a disease in which the coronary artery is occluded by, for example, thrombosis, and blood flow to the myocardium under the coronary artery is obstructed, leading to myocardial necrosis. Therefore, acute myocardial infarction is treated through a therapy in which blood flow is restored by recanalization of the occluded coronary artery, together with treatment of arrhythmia, such as ventricular fibrillation (hereinafter the therapy may be referred to as "myocardial ischemia-reperfusion therapy"). Myocardial ischemia-reperfusion therapies include a thrombolytic therapy using, for example, t-PA, and PTCA using a balloon catheter. When such a myocardial ischemia-reperfusion therapy is performed within six hours after the onset of myocardial infarction, the therapy achieves high survival rate and is effective.

However, it has been known that myocardial ischemia-reperfusion causes inflammatory response due to, for example, free radicals (e.g., active oxygen), vascular endothelial cell injury, or neutrophil activation, resulting in additional damage to the myocardium. Thus, demand has arisen for development of a drug that reduces the incidence of myocardial ischemia-reperfusion injury.

Adenosine is known as a compound that reduces the incidence of myocardial ischemia-reperfusion injury (see Non-Patent Document 1). Exogenous adenosine increases coronary blood flow via the $A_2$ receptor, and inhibits generation of free radicals from activated neutrophils. In addition, exogenous adenosine activates the $A_1$ receptor, thereby suppressing an increase in adrenergic-β-receptor-mediated myocardial contractility, an increase in amount of $Ca^{2+}$ influx into the myocardium, or an increase in amount of released norepinephrine. By virtue of these effects, adenosine suppresses myocardial injury caused by myocardial ischemia, or myocardial ischemia-reperfusion injury.

However, adenosine has a short half life (<10 sec) in blood, and thus exhibits a short duration of action. Therefore, expression of the myocardial protection effect of adenosine through peripheral intravenous injection requires administration of a large amount of adenosine for a long period of time (30 minutes to 1 hour) (see Non-Patent Document 2). Meanwhile, adenosine is known to cause side effects such as lowered blood pressure or heart rate. Such adverse effects of adenosine on hemodynamics through administration thereof to a myocardial infarction patient are not desired.

At present, adenosine is used in clinical practice as a diagnostic aid for cardiac diseases (see Non-Patent Document 3).
Non-Patent Document 1: Drug Development Research, vol. 28, 432-437, 1993
Non-Patent Document 2: J. Am. Coll. Cardiol., 1775-1780, 2005
Non-Patent Document 3: JAPIC Iryo-yo Iyakuhin-shu (Data on Drugs for Medical Use) 2007, edited and published by Japan Pharmaceutical Information Center, Sep. 1, 2006, pp. 88-90

DISCLOSURE OF THE INVENTION

Problems to be Solved by the Invention

An object of the present invention is to provide a preventive and/or therapeutic drug for myocardial infarction or myocardial ischemia-reperfusion injury, which contains adenosine as an active ingredient, and in which side effects of adenosine are reduced so as to utilize the excellent effect of adenosine in reducing the incidence of myocardial ischemia-reperfusion injury.

Means for Solving the Problems

The present inventors have conducted extensive studies, and as a result have found that when adenosine is retained in a lipid membrane structure, the lipid membrane structure retaining adenosine exhibits excellent pharmacological effects of adenosine and reduced side effects of adenosine, and can serve as a preventive and/or therapeutic drug for myocardial infarction or myocardial ischemia-reperfusion injury. The present invention has been accomplished on the basis of this finding.

Accordingly, the present invention provides the following.
(1) A preventive and/or therapeutic drug for myocardial infarction or myocardial ischemia-reperfusion injury, the drug containing a lipid membrane structure retaining adenosine.
(2) Use of a lipid membrane structure retaining adenosine for producing a preventive and/or therapeutic drug for myocardial infarction or myocardial ischemia-reperfusion injury.
(3) Provision of a lipid membrane structure retaining adenosine for prevention and/or treatment of myocardial infarction or myocardial ischemia-reperfusion injury.
(4) A method for prevention and/or treatment of myocardial infarction or myocardial ischemia-reperfusion injury, the method comprising administering a lipid membrane structure retaining adenosine to a subject in need thereof.

Effects of the Invention

As shown in the Examples hereinbelow, the preventive and/or therapeutic drug for myocardial infarction or myocardial ischemia-reperfusion injury of the present invention exhibits excellent effect of reducing the incidence of myocardial ischemia-reperfusion injury, and reduced side effects of adenosine (e.g., lowering of blood pressure or heart rate). Particularly, the lipid membrane structure retaining adenosine of the present invention significantly reduces infarct size and the incidence of ventricular fibrillation through administration before ischemia or ischemia-reperfusion, although administration of adenosine only does not exhibit such an efficacy. Therefore, lipid membrane structure retaining adenosine of the present invention is useful as a preventive and/or therapeutic drug for myocardial infarction or myocardial ischemia-reperfusion injury. Particularly, the lipid membrane structure retaining adenosine is useful as a preventive and/or therapeutic drug for myocardial ischemia-reperfusion injury.

BEST MODES FOR CARRYING OUT THE INVENTION

Figure 1:
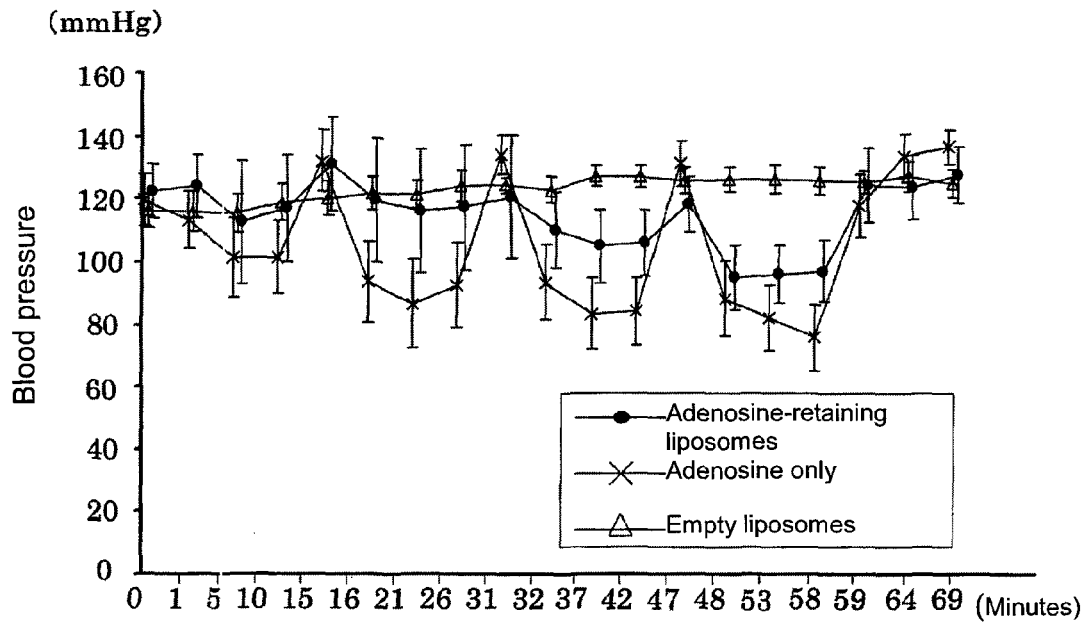
FIG. 1 is a graph showing blood pressure as determined upon drug administration.

The preventive and/or therapeutic drug for myocardial infarction or myocardial ischemia-reperfusion injury of the present invention contains a lipid membrane structure retaining adenosine.

The Lipid membrane structure retaining adenosine of the present invention contains adenosine, and a lipid membrane structure which retains adenosine.

The lipid membrane structure of the present invention contains a phospholipid and a sterol, and optionally contains, for example, a blood-circulatory lipid derivative or a temperature-change-sensitive lipid derivative.

Examples of the phospholipid include phosphatidylethanolamine, phosphatidylcholine, phosphatidylserine, phosphatidylinositol, phosphatidylglycerol, cardiolipin, sphingomyelin, plasmalogen, and phosphatidic acid. These phospholipids may be employed singly or in combination of two or more species. In the present invention, the phospholipid is preferably phosphatidylcholine. No particular limitation is imposed on the fatty acid residue of such a phospholipid, and the fatty acid residue may be a C12 to C18 saturated or unsaturated fatty acid residue. Examples of preferred fatty acid residues include a myristoyl group, a palmitoyl group, an oleoyl group, a stearoyl group, and a linoleyl group. In the present invention, the phospholipid is particularly preferably hydrogenated soybean lecithin.

Examples of the sterol include cholesterol, dihydrocholesterol, cholesterol succinate, cholestanol, lanosterol, dihydrolanosterol, desmosterol, stigmasterol, sitosterol, campesterol, brassicasterol, zymosterol, and ergosterol. These sterols may be employed singly or in combination of two or more species. In the present invention, the sterol is preferably cholesterol or cholestanol.

When a blood-circulatory lipid derivative, which is an optional component, is contained in the lipid membrane structure, there can be realized a reduction in percent entrapment of the lipid membrane structure by the reticuloeadothelial tissue of, for example, the liver or spleen, and retention of the lipid membrane structure in blood can be improved. When a temperature-change-sensitive lipid derivative is contained in the lipid membrane structure, the releasability or targeting effect of adenosine retained in the lipid membrane structure can be enhanced.

No particular limitation is imposed on the blood-circulatory lipid derivative employed, so long as it can impart a blood-circulatory function to the lipid membrane structure and can form the lipid membrane structure. Examples of the blood-circulatory lipid derivative include glycophorin, ganglioside GM1, phosphatidylinositol, ganglioside GM3, a glucuronic acid derivative, a glutamic acid derivative, a polyglycerin-phospholipid derivative, and a polyethylene glycol derivative. Examples of the polyethylene glycol derivative include N-{carbonyl-methoxypolyethylene glycol-2000}-1,2-dipalmitoyl-sn-glycero-3-phosphoethanolamine, N-{carbonyl-methoxypolyethylene glycol-5000}-1,2-dipalmitoyl-sn-glycero-3-phosphoethanolamine, N-{carbonyl-methoxypolyethylene glycol-750}-1,2-distearoyl-sn-glycero-3-phosphoethanolamine, N-{carbonyl-methoxy-polyethylene glycol-2000}-1,2-distearoyl-sn-glycero-3-phosphoethanolamine, and N-{carbonyl-methoxy-polyethylene glycol-5000}-1,2-distearoyl-sn-glycero-3-phosphoethanolamine. These polyethylene glycol derivatives may be employed singly or in combination of two or more species. Of the aforementioned blood-circulatory lipid derivatives, a polyethylene glycol derivative is preferred.

No particular limitation is imposed on the temperature-change-sensitive lipid derivative employed, so long as it can impart a temperature-change-sensitive function to the lipid membrane structure and can form the lipid membrane structure. Examples of the temperature-change-sensitive lipid derivative include dipalmitoylphosphatidylcholine.

In the lipid membrane structure of the present invention, the ratio by mole of a phospholipid to a sterol is preferably 1:4 to 4:1, more preferably 3:2 to 2:3.

When the lipid membrane structure contains, as a component, a blood-circulatory lipid derivative, a temperature-change-sensitive lipid derivative, or the like, the ratio by mole of the total of a phospholipid and a sterol to a blood-circulatory lipid derivative, a temperature-change-sensitive lipid derivative, or the like is preferably 10:0.01 to 10:2, more preferably 10:0.1 to 10:0.5.

No particular limitation is imposed on the amount of adenosine contained in the lipid membrane structure retaining adenosine of the present invention, so long as the amount is enough to express the effect of adenosine in reducing the incidence of myocardial ischemia-reperfusion injury, or the effect of adenosine in prevention and/or treatment of myocardial infarction. The amount of adenosine may be appropriately determined in consideration of, for example, the form of the lipid membrane structure, or the symptom, sex, age, or body weight of a subject in need thereof. For example, the ratio by mole of adenosine to the total lipid content of the phospholipid and sterol contained in the lipid membrane structure is preferably 0.01 to 2, more preferably 0.05 to 0.2.

The lipid membrane structure of the lipid membrane structure retaining adenosine of the present invention may be in the form of a simple mixture of a phospholipid, a sterol, and, for example, an optional blood-circulatory lipid derivative or temperature-change-sensitive lipid derivative. Alternatively, the lipid membrane structure may be formed from a combination of a phospholipid, a sterol, and, for example, an optional blood-circulatory lipid derivative.

As used herein, the term "lipid membrane structure" refers to a particle having a membrane structure in which polar groups of a polar lipid are arranged to face an aqueous phase of an interface. Examples of such a lipid membrane structure include a liposome, a micelle, and a microemulsion.

No particular limitation is imposed on the form of the lipid membrane structure, and the lipid membrane structure may be in the form of, for example, a dry lipid mixture, an aqueous solvent dispersion, or a dried or frozen product of the dispersion.

Examples of the aqueous solvent dispersion form of the lipid membrane structure include a liposome such as a single-membrane liposome or a multi-layer liposome; an emulsion such as an O/W emulsion or a W/O/W emulsion; a micelle such as a spherical micelle or a thread-like micelle; and an amorphous layered structure. Of these, a liposome form is preferred. No particular limitation is imposed on the size of the dispersed lipid membrane structure. For example, when the lipid membrane structure is in the form of liposomes or emulsion, the structure has a particle size of 50 nm to 5 µm, whereas when the lipid membrane structure is in the form of spherical micelles, the structure has a particle size of 5 to 100 nm. When the lipid membrane structure is in the form of thread-like micelles or amorphous layered structure, the structure is preferably formed of layers each having a thickness of 5 to 10 nm. In the present invention, the lipid membrane structure is preferably in the form of liposomes, particularly preferably liposomes having a particle size of 200 nm or less.

Next will be described embodiments of the method for producing various forms of the lipid membrane structure.

I) The lipid membrane structure in the form of dry mixture may be produced by, for example, temporarily dissolving all the components of the lipid membrane structure in an organic solvent (e.g., chloroform), and then drying the resultant solution to solid under reduced pressure by means of an evaporator, or subjecting the solution to spray drying by means of a spray dryer.

II) The lipid membrane structure in the form of aqueous solvent dispersion may be produced by adding the aforementioned dry mixture to an aqueous solvent, and then emulsifying the resultant mixture by means of, for example, an emulsifier (e.g., a homogenizer), an ultrasonic emulsifier, or a high-pressure jet emulsifier. Alternatively, the lipid membrane structure in the form of aqueous solvent dispersion may be produced through a method well-known as a liposome production method (e.g., the reverse-phase evaporation method). When control of the size of the lipid membrane structure is required, extrusion (extrusion filtration) may be carried out under high pressure by means of, for example, a membrane filter having pores of uniform size.

No particular limitation is imposed on the composition of an aqueous solvent (dispersion medium) employed. Examples of the aqueous solvent which may be employed include buffers such as phosphate buffer, citrate buffer, and phosphate buffered saline; physiological saline; and culture media for cell culture. Such an aqueous solvent (dispersion medium), in which the lipid membrane structure can be stably dispersed, may further contain, for example, a sugar (or an aqueous solution thereof), or a polyhydric alcohol (or an aqueous solution thereof). Examples of the sugar include monosaccharides such as glucose, galactose, mannose, fructose, inositol, ribose, and xylose; disaccharides such as lactose, sucrose, cellobiose, trehalose, and maltose; trisaccharides such as raffinose and melezitose; polysaccharides such as cyclodextrin; and sugar alcohols such as erythritol, xylitol, sorbitol, mannitol, and maltitol. Examples of the polyhydric alcohol include glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, and 1,3-butylene glycol. In order to stably store the lipid membrane structure dispersed in such an aqueous solvent (dispersion medium) for a long period of time, preferably, the amount of electrolytes in the aqueous solvent (dispersion medium) is reduced to a minimum possible level, from the viewpoint of physical stability (e.g., from the viewpoint of preventing aggregation). From the viewpoint of chemical stability of lipid, preferably, the pH of the aqueous solvent (dispersion medium) is adjusted to fall within a range of 3 to 8 (preferably 5 to 7) (i.e., from slightly acidic to around neutral), or dissolved oxygen is removed through nitrogen bubbling.

No particular limitation is imposed on the sugar or polyhydric alcohol concentration of the aqueous solvent in which the lipid membrane structure is dispersed. However, for example, the sugar (or aqueous solution thereof) concentration is preferably 2 to 20% (W/V), more preferably 5 to 10% (W/V), and the polyhydric alcohol (or aqueous solution thereof) concentration is preferably 1 to 5% (W/V), more preferably 2 to 2.5% (W/V). When the aqueous solvent (dispersion medium) employed is a buffer, the buffering agent concentration of the buffer is preferably 5 to 50 mM, more preferably 10 to 20 mM. No particular limitation is imposed on the lipid membrane structure concentration of the aqueous solvent (dispersion medium), but the total lipid concentration (the amounts of components of the lipid membrane structure, including phospholipid, sterol, and optional blood-circulatory lipid derivative) of the dispersion is preferably 0.2 to 50 mM, more preferably 1 to 10 mM.

III) A dried or frozen product of the lipid membrane structure dispersed in any of the aforementioned aqueous solvents may be produced by subjecting the aqueous solvent dispersion of the lipid membrane structure to a common drying or freezing process (e.g., lyophilization or spray drying). When the above-produced aqueous solvent dispersion of the lipid membrane structure is further dried, the lipid membrane structure can be stored for a long period of time. When an aqueous solution containing adenosine is added to the thus-dried lipid membrane structure, advantageously, the lipid mixture is effectively mixed with water, and thus adenosine can be effectively retained in the lipid membrane structure.

In the case where the aqueous solvent dispersion of the lipid membrane structure is lyophilized or spray-dried, when a sugar (e.g., a monosaccharide such as glucose, galactose, mannose, fructose, inositol, ribose, or xylose; a disaccharide such as lactose, sucrose, cellobiose, trehalose, or maltose; a trisaccharide such as raffinose or melezitose; a polysaccharide such as cyclodextrin; or a sugar alcohol such as erythritol, xylitol, sorbitol, mannitol, or maltitol) or an aqueous solution thereof is employed, the lipid membrane structure can be stably stored for a long period of time. In the case where the aqueous solvent dispersion of the lipid membrane structure is frozen, when any of the aforementioned sugars (or an aqueous solution thereof), or a polyhydric alcohol (e.g., glycerin, diglycerin, polyglycerin, propylene glycol, polypropylene glycol, ethylene glycol, diethylene glycol, triethylene glycol, polyethylene glycol, ethylene glycol monoalkyl ether, diethylene glycol monoalkyl ether, or 1,3-butylene glycol) or an aqueous solution thereof is employed, the lipid membrane structure can be stably stored for a long period of time. Such a sugar and polyhydric alcohol may be employed in combination.

Next will be described the lipid membrane structure retaining adenosine of the present invention.

The lipid membrane structure retaining adenosine may be in the form of a simple mixture of adenosine, a phospholipid, a sterol, and, for example, an optional blood-circulatory lipid derivative. Alternatively, the lipid membrane structure retaining adenosine may be in the form of a mixture of adenosine and a lipid membrane structure formed of a phospholipid, a sterol, and, for example, an optional blood-circulatory lipid derivative, in combination. Yet alternatively, the lipid membrane structure retaining adenosine may be in a form in which adenosine is present in a lipid membrane of the lipid membrane structure, on the surface cf the lipid membrane, inside of the lipid membrane structure, in a lipid layer of the structure, and/or on the surface of the lipid layer. When the lipid membrane structure is in the form of microparticles (e.g., liposomes), adenosine may be encapsulated in the microparticles.

In the present invention, in consideration of administration of the lipid membrane structure retaining adenosine, the structure is preferably in such a form that adenosine is not exposed to blood. Specifically, the lipid membrane structure retaining adenosine is preferably in a form in which adenosine is present in a lipid membrane of the lipid membrane structure, inside of the lipid membrane structure, and/or in a lipid layer of the structure. Particularly preferably, the lipid membrane structure retaining adenosine is in the form of liposomes in which adenosine is encapsulated.

Similar to the case of the aforementioned lipid membrane structure, the lipid membrane structure retaining adenosine may be in the form of, for example, a dry mixture, an aqueous solvent dispersion, or a dried or frozen product of the dispersion.

Next will be described methods for producing various forms of the lipid membrane structure retaining adenosine.

1) The lipid membrane structure retaining adenosine in the form of aqueous solvent dispersion containing the lipid membrane structure and adenosine may be produced through several known methods. In consideration of the mode for retaining adenosine in the lipid membrane structure, the properties of the mixture, etc., the production method may be appropriately selected from among the below-described methods 1-1 to 1-4.

1-1) Production Method 1

In production method 1, the components of the lipid membrane structure are temporarily dissolved in an organic solvent; the organic solvent is removed through evaporation; and an aqueous solvent containing adenosine is added to the resultant dry product, followed by emulsification. For control of size (particle size), extrusion (extrusion filtration) may be carried out under high pressure by means of a membrane filter having pores of uniform size. This method is applicable to adenosine, which is difficult to dissolve in an organic solvent but is dissolved in an aqueous solvent. This method is advantageous in that, when the lipid membrane structure is in the form of liposomes, adenosine can also be retained in the internal aqueous phase of the structure.

1-2) Production Method 2

In production method 2, an aqueous solvent containing adenosine is added to the lipid membrane structure in the form of, for example, liposomes, emulsion, micelles, or layered structure which has already been dispersed in an aqueous solvent. In this method, adenosine is added to the lipid membrane structure which has already been prepared. Therefore, adenosine may fail to enter inside the lipid membrane structure and may be present on (bound to) the surface of the lipid membrane structure. However, when the pH of the dispersion medium for liposomes is adjusted to fall within a neutral range so that a pH gradient is formed between the inside and outside of the liposomes, adenosine can be retained in the liposomes at a higher concentration. As has been known, when production method 2 is applied to the lipid membrane structure in the form of liposomes, adenosine is sandwiched between liposome particles; i.e., a sandwich structure (generally called "complex") is formed. In this production method, since an aqueous dispersion containing only the lipid membrane structure is produced in advance, no attention must be paid to, for example, degradation of adenosine during emulsification, and size (particle size) is readily controlled. Therefore, the lipid membrane structure retaining adenosine can be readily produced through production method 2, as compared with the case of production method 1.

1-3) Production Method 3

In production method 3, the lipid membrane structure dispersed in an aqueous solvent is dried, and an aqueous solvent containing adenosine is added to the resultant dry product. Production method 3 differs from production method 2 in terms of mode of presence of the lipid membrane structure and adenosine. In production method 3, the lipid membrane structure is temporarily dispersed in an aqueous solvent, and the resultant dispersion is dried. At this stage of the method, the lipid membrane structure is present in the form of a solid lipid membrane fragment. In order to cause such a lipid membrane fragment to be present in a solid form, preferably, as described above, a sugar (or an aqueous solution thereof) (more preferably, sucrose or lactose (or an aqueous solution thereof)) is added to the aqueous solvent employed. When an aqueous solvent containing adenosine is added to the lipid membrane fragment present in a solid form, the lipid membrane fragment is rapidly invaded by water and hydrated, to thereby reconstitute the lipid membrane structure. In this case, the thus-reconstituted lipid membrane structure retains adenosine within its structure.

Production method 2 greatly differs from production method 3 in that adenosine may fail to enter inside the lipid membrane structure and may be bound to the surface of the lipid membrane structure. That is, in the case of production method 3, the entirety or a portion of adenosine is incorporated in the inside of the lipid membrane structure. In production method 3, since a dispersion containing only the lipid membrane structure is produced in advance, no attention must be paid to degradation of adenosine during emulsification, and size (particle size) is readily controlled. Thus, the lipid membrane structure retaining adenosine is readily produced through production method 3, as compared with the case of production method 1. In addition, in production method 3, the lipid membrane structure is temporarily subjected to lyophilization or spray drying. Therefore, this method is advantageous in that, for example, storage stability of the drug formulation (adenosine-containing lipid membrane structure formulation) is readily assured, the size (particle size) of a dried formulation can be restored after rehydration of the dried formulation with an aqueous solution of adenosine, and adenosine is readily retained inside the lipid membrane structure.

1-4) Other Methods

An aqueous solvent dispersion of a mixture of the lipid membrane structure and adenosine may be produced through a method well known as a liposome production method (e.g., the reverse-phase evaporation method). For control of size (particle size), extrusion (extrusion filtration) may be carried out under high pressure by means of a membrane filter having pores of uniform size.

2) When the aforementioned aqueous solvent dispersion of the lipid membrane structure-adenosine mixture is further dried, lyophilization, spray drying, or a similar technique may be employed. In this case, the aqueous solvent employed is preferably a solvent containing any of the aforementioned sugars (or an aqueous solution thereof) (more preferably, sucrose or lactose (or an aqueous solution thereof)). When the aqueous solvent dispersion of the lipid membrane structure-adenosine mixture is further frozen, a common freezing technique may be employed. In this case, the aqueous solvent employed is preferably a solvent containing a sugar (or an aqueous solution thereof) or a polyhydric alcohol (or an aqueous solution thereof).

3) When a blood-circulatory function or a temperature-sensitive function is imparted to the lipid membrane structure, preferably, a blood-circulatory lipid derivative or a temperature-change-sensitive lipid derivative is caused to be present on the surface of the lipid membrane of the lipid membrane structure. In this case, the lipid membrane structure retaining adenosine can be produced through any of the following procedures: (i) a solution (or dispersion) prepared by dissolving (or dispersing) adenosine and a blood-circulatory lipid derivative or the like in an aqueous solvent is added to a lipid membrane structure formed of, for example, a phospholipid and a sterol; (ii) a solution (or dispersion) prepared by dissolving (or dispersing) a blood-circulatory lipid derivative or the like in an aqueous solvent is added to a lipid membrane structure formed of, for example, adenosine, a phospholipid, and a sterol; (iii) a solution prepared by dissolving adenosine in an aqueous solvent is added to a lipid membrane structure formed of, for example, a phospholipid, a sterol, and a blood-circulatory lipid derivative; and (iv) a solution prepared by dissolving adenosine in an aqueous solvent is added to a lipid membrane structure formed of, for example, a phospholipid and a sterol, followed by addition of a solution (or dispersion) prepared by dissolving (or dispersing) a blood-circulatory lipid derivative or the like in an aqueous solvent. For control of size (particle size), extrusion (extrusion filtration) may be carried out under high pressure by means of a membrane filter having pores of uniform size. The resultant product may be provided in a dry form in a manner similar to that described above in 2).

The thus-produced lipid membrane structure retaining adenosine of the present invention realizes utilization of the effect of adenosine in reducing the incidence of myocardial ischemia-reperfusion injury, and is useful as a preventive and/or therapeutic agent for myocardial infarction or myocardial ischemia-reperfusion injury. Particularly, when, in the lipid membrane structure retaining adenosine, adenosine is present in a lipid membrane of the lipid membrane structure, inside of the lipid membrane structure, or in a lipid layer of the structure, and a blood-circulatory lipid derivative is present on the surface of the lipid membrane, the lipid membrane structure retaining adenosine is useful as a preventive and/or therapeutic drug for myocardial infarction or myocardial ischemia-reperfusion injury.

The lipid membrane structure retaining adenosine of the present invention may be administered to a subject in need thereof for reducing the incidence of myocardial ischemia-reperfusion injury or for prevention and/or treatment of myocardial infarction. The lipid membrane structure retaining adenosine may be parenterally or orally administered. No particular limitation is imposed on the parenteral dosage form, so long as the dosage form is a generally known one; for example, injection, eye drop, ointment, or suppository. No particular limitation is imposed on the oral dosage form, so long as the dosage form is a generally known one; for example, tablet, powder, or granules. In the present invention, parenteral administration is preferred, with injection being particularly preferred. Preferably, intravenous injection, intra-arterial injection, drip infusion, or the like is carried out.

EXAMPLES

The present invention will next be described by way of examples, which should not be construed as limiting the invention thereto.

Example 1

1. Preparation of Lipid Mixture

Hydrogenated soybean lecithin (LIPOID S PC-3, product of Nisshin Oil Mills, Ltd.) and cholesterol (product of Wako Pure Chemical Industries, Ltd.) were weighed (ratio by mole=6:4), and these materials were dissolved in chloroform. The resultant chloroform solution was pressure-filtered (filter: PVDF GV (0.22 µm), product of Millipore). The filtrate was concentrated and dried to solid under reduced pressure at about 80° C., and the resultant product was further allowed to stand overnight under reduced pressure.

2. Preparation of Adenosine Solution

Adenosine (product of SIGMA) was dissolved in a 300 mM aqueous citric acid (pH 3.0), to thereby prepare a 60 mg/mL adenosine solution, and the solution was pressure-filtered (filter: PVDF GV (0.22 µm), product of Millipore).

3. Preparation of Liposomes 3-1. Preparation of Adenosine-Retaining Liposomes

The adenosine solution was added to the above-prepared lipid mixture, and the mixture was subjected to ultrasonic treatment at 65° C. (preset temperature) for 30 minutes, to thereby yield a crude emulsion having a lipid concentration of 130 mM or 260 mM. The emulsion was subjected to sizing under pressure of nitrogen gas by means of a filter maintained at 65° C. (preset temperature) (filter: polycarbonate, 0.2 µm (five times), 0.1 µm (five times), and 0.05 µm (thrice)), to thereby yield a liposome liquid (method I).

A 300 mM aqueous citric acid whose pH had been adjusted to about 3 with sodium hydroxide was added to the above-prepared lipid mixture, and the mixture was subjected to ultrasonic treatment at 65° C. (preset temperature) for 30 minutes, to thereby yield a crude emulsion having a lipid concentration of 260 mM. The emulsion was subjected to sizing under pressure of nitrogen gas by means of a filter maintained at 65° C. (preset temperature) (filter: polycarbonate, 0.2 µm (five times), 0.1 µm (five times), and 0.05 µm (thrice)). To the resultant product was added a two-fold amount of the adenosine solution, to thereby yield a liposome liquid (method II).

The liposome liquid prepared through method I or method II was heated to 60° C. (preset temperature), and a 2M sodium hydroxide solution containing 300 mM sodium citrate was added to the liposome liquid, to thereby adjust the pH of the mixture to 5 to 6. After pH adjustment, DSPE-PEG2000 was added to the mixture so that the ratio by mole of DSPE-PEG2000 to the lipid mixture was 0.031, followed by incubation at 60° C. (preset temperature) for 30 minutes. The resultant suspension of adenosine-retaining liposomes was diluted with a five-fold amount of a 5% glucose solution, and then ultracentrifugation was carried out ($3\times10^5$ g, 4° C., 60 minutes). To the thus-obtained pellets was added a 9% sucrose solution containing 50 mM sodium lactate (pH of the solution: about 5) or a 9% sucrose solution containing 100 mM sodium lactate (pH of the solution: about 5) for resuspension. The resultant suspension was allowed to stand overnight at 5° C., and then centrifugation was carried out (10,000 rpm, 4° C., 10 minutes), to thereby remove precipitated adenosine. The resultant product was diluted with a five-fold amount of a 5% glucose solution, and then ultracentrifugation was carried out ($3\times10^5$ g, 4° C., 60 minutes). To the thus-obtained pellets was added a 9% sucrose solution containing 50 mM sodium lactate (pH of the solution: about 5) or a 9% sucrose solution containing 100 mM sodium lactate so as to attain an adenosine concentration of 1.5 mg/mL, to thereby prepare adenosine-retaining liposomes (i.e., a sample for evaluation).

3-2. Preparation of Empty Liposomes

A 300 mM aqueous citric acid whose pH had been adjusted to about 3 with sodium hydroxide was added to the above-prepared lipid mixture, and the mixture was subjected to ultrasonic treatment at 65° C. (preset temperature) for 30 minutes, to thereby yield a crude emulsion having a lipid concentration of 260 mM. The emulsion was subjected to sizing under pressure of nitrogen gas by means of a filter maintained at 65° C. (preset temperature) (filter: polycarbonate, 0.2 μm (thrice), 0.1 μm (five times), and 0.05 μm (thrice)), to thereby yield a liposome liquid.

A 2M sodium hydroxide solution containing 300 mM sodium citrate was added to the liposome liquid, to thereby adjust the pH of the mixture to 5 to 6. After pH adjustment, DSPE-PEG2000 was added in the form of a 9% sucrose solution to the mixture so that the ratio by mole of DSPE-PEG2000 to the lipid mixture was 0.031, followed by incubation at 60° C. (preset temperature) for 30 minutes. The resultant suspension was diluted with a five-fold amount of a 5% glucose solution, and then ultracentrifugation was carried out ($3 \times 10^5$ g, 4° C., 60 minutes). To the thus-obtained pellets was added a 9% sucrose solution containing 100 mM sodium lactate (pH of the solution: about 5) for resuspension, to thereby prepare empty liposomes (i.e., a control sample).

4. Quality Test of Liposomes 4-1. Determination Method

The mean particle size of the thus-prepared liposomes (adenosine-retaining liposomes or empty liposomes); i.e., liposomes employed for Test Examples, was determined by means of NICOMP 380 ZLS.

4-2. Results of Determination

Data of the thus-determined mean particle size are shown below.

TABLE 1

| | Mean particle size (nm) | |
| --- | --- | --- |
| | Hemodynamic test | Infarction test |
| Adenosine-retaining liposomes | 117.5 to 126.2 | 109.4 to 117.5 |
| Empty liposomes | 105.6 to 110.6 | 142.8 |

Test Example 1

Hemodynamic Test

Male SD rats (nine weeks old, body weight: 270 g to 320 g, supplied by Japan SLC, Inc.) were employed. Each of the rats was anesthetized with pentobarbital sodium (30 mg/kg, intraperitoneal injection) and then fixed in the dorsal position. A tube was orally inserted into the trachea, and artificial ventilation was carried out by means of a ventilator for small animals. A catheter (INTRAMEDIC Polyethylene Tubing PE50, CLAY ADAMS) was inserted into the femoral artery and the femoral vein, and systolic blood pressure, diastolic blood pressure, and mean blood pressure were measured in the femoral artery. Heart rate was measured by means of an electrocardiograph. A drug sample was injected through the catheter indwelled in the femoral vein by means of a syringe pump (Model PHD 4400, HARVARD). Specifically, after stabilization of hemodynamics, empty liposomes (n=8), adenosine only (n=8), and adenosine-retaining liposomes (n=8) were injected transvenously, respectively.

In an empty liposome group, injection was carried out at 0.05 mL/minute for 10 minutes (one minute, five minutes, and 10 minutes after initiation of injection, blood pressure and heart rate were evaluated), and, for five minutes after completion of injection, blood pressure and heart rate were evaluated. Thereafter, evaluation was carried out in a manner similar to that described above at an injection rate of 0.1 mL/minute, 0.2 mL/minute, or 0.4 mL/minute. In an adenosine-only group or an adenosine-retaining liposome group, injection was initiated at 0.05 mL/minute (225 μg/kg/minute as reduced to adenosine), and cumulative administration was carried out through the same protocol as in the case of the empty liposome group.

Figure 2:
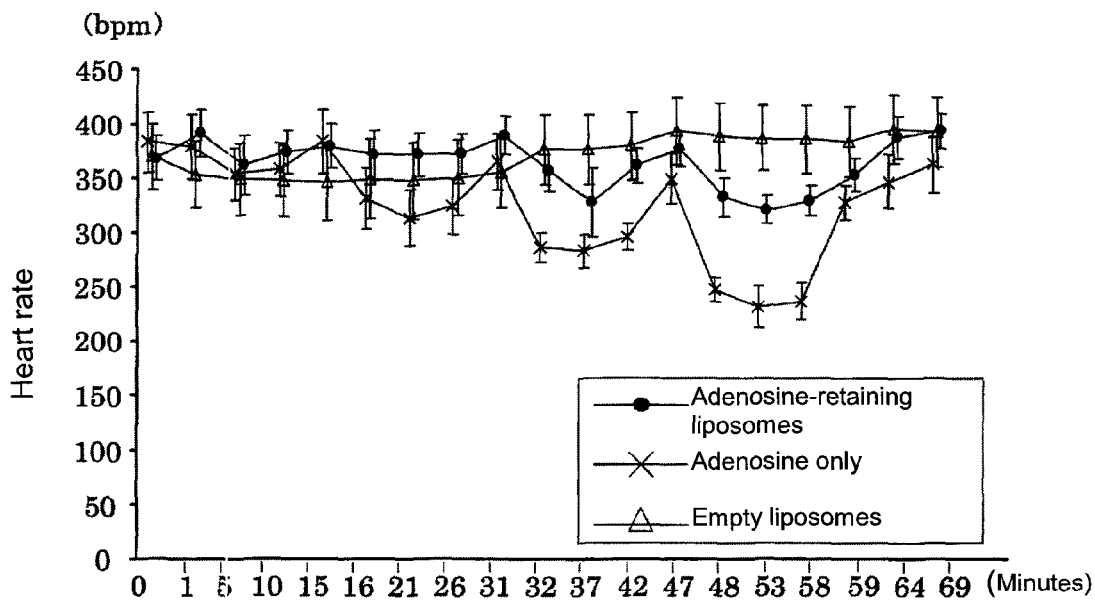
FIG. 2 is a graph showing heart rate as determined upon drug administration.

The results are shown in FIGS. 1 and 2. As shown in FIGS. 1 and 2, no significant change in hemodynamics was observed in the empty liposome group. Ten minutes after initiation of adenosine injection at 225 μg/kg/minute, in the adenosine-only group, mean blood pressure and heart rate were found to be 101±12 mmHg and 357±25 bpm, respectively, whereas in the adenosine-retaining liposome group, mean blood pressure and heart rate were found to be 117±17 mmHg and 373±20 bpm, respectively. Ten minutes after initiation of adenosine injection at 450 μg/kg/minute, in the adenosine-only group, mean blood pressure and heart rate were found to be 93±14 mmHg and 324±25 bpm, respectively, whereas in the adenosine-retaining liposome group, mean blood pressure and heart rate were found to be 117±20 mmHg and 372±18 bpm, respectively. Ten minutes after initiation of adenosine injection at 900 μg/kg/minute, in the adenosine-only group, mean blood pressure and heart rate were found to be 84±11 mmHg and 296±12 bpm, respectively, whereas in the adenosine-retaining liposome group, mean blood pressure and heart rate were found to be 106±11 mmHg and 361±16 bpm, respectively. Ten minutes after initiation of adenosine injection at 1,800 μg/kg/minute, in the adenosine-only group, mean blood pressure and heart rate were found to be 75±11 mmHg and 236±17 bpm, respectively, whereas in the adenosine-retaining liposome group, mean blood pressure and heart rate were found to be 97±10 mmHg and 328±13 bpm, respectively. Thus, in the adenosine-retaining liposome group, reduction in blood pressure or heart rate was significantly suppressed, as compared with the case of the adenosine-only group.

Test Example 2

Ischemia-Reperfusion Test (Rat)

1) Test method

Similar to the case of the hemodynamic test, male SD rats were employed. Each of the rats was anesthetized and artificially ventilated, and then thoracotomy was carried out at the thoracic sidewall. The left anterior descending coronary artery (LAD) was ligated by means of a suturing needle with suture for 30 minutes, and then blood flow was restored, to thereby prepare an ischemia-reperfusion model. A drug sample was injected through a catheter (INTRAMEDIC Polyethylene Tubing PE50, CLAY ADAMS) indwelled in the femoral vein.

In this test, an adenosine-retaining liposome group were divided into two groups: a group received adenosine-retaining liposomes before ischemia (injected for 10-minute before ischemia), and a group received adenosine-retaining liposomes before reperfusion (injected for 10-minute initiated 5 minutes before reperfusion). In the other groups, injection was carried out before ischemia (injected for 10-minute before ischemia). Specifically, the test was carried out in the following groups (dose): 1) control group (saline, 0.2 mL/minute, n=7); 2) empty liposome group (0.2 mL/minute, n=9); 3) adenosine-only group (0.2 mL/minute (900 μg/kg/minute), n=8); 4) group received adenosine-retaining liposome before ischemia (0.2 mL/minute (900 μg/kg/minute), n=10); and 5) group received adenosine-retaining liposome before reperfusion (0.2 mL/minute (900 μg/kg/minute), n=10).

2) Method for Measuring Myocardial Infarct Size

Each of the rats was anesthetized 72 hours after reperfusion, and then thoracotomy was carried out again. Subsequently, the above-ligated portion was re-ligated by means of a suturing needle with suture. Thereafter, a 2% Evans blue solution (1 to 2 mL) was injected through the catheter indwelled in the femoral vein, to thereby stain a non-ischemic portion, and then the heart was extirpated. The left ventricle was divided in four specimens in a minor axis direction, and the specimens were stained with a 1% TTC solution at 37° C. for five minutes. After staining, the specimens were photographed, and an ischemic risk area (non-Evans blue-stained area) and an infarct area (non-TTC-stained area) were determined by means of Win ROOF Version 5.5 (product of Mitani Corporation). Infarct size was calculated by dividing the infarct area by the ischemic risk area.

3) Test Results

Figure 3:
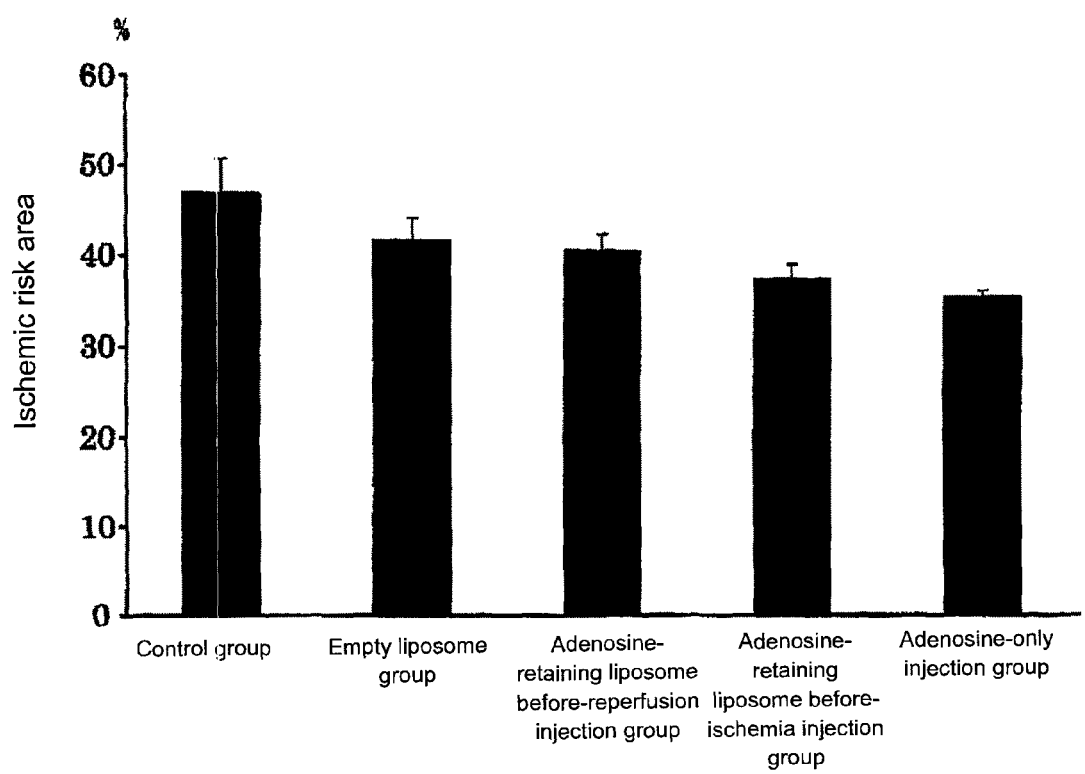
FIG. 3 is a graph showing the effect of a drug on ischemic risk area upon administration of the drug to an ischemia-reperfusion model rat.
Figure 4:
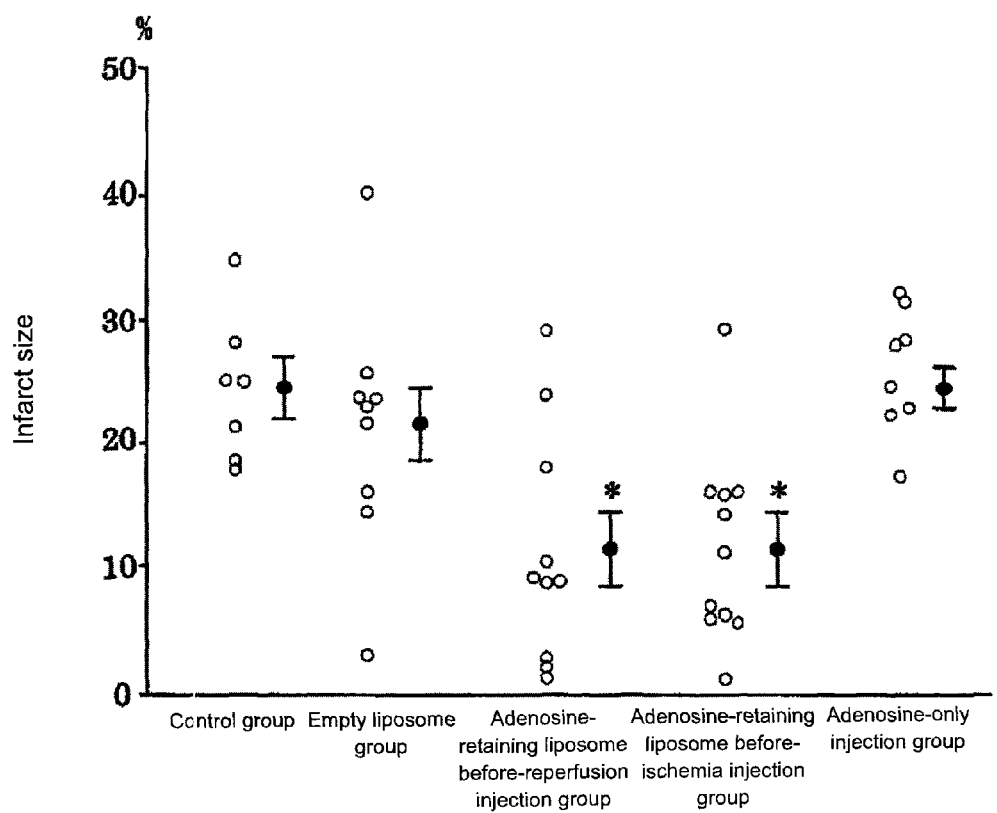
FIG. 4 is a graph showing the effect of a drug on infarct size upon administration of the drug to an ischemia-reperfusion model rat.

The results are shown in FIGS. 3 and 4. As shown in FIG. 3, the following data of ischemic risk area were obtained: control group: 45.4±3.5%, empty liposome group: 41.5±2.6%, adenosine-only group: 35.5±2.7%, adenosine-retaining liposome group (injection before ischemia): 37.2±1.6%, and adenosine-retaining liposome group (injection before reperfusion): 40.5±1.7%. Thus, no significant difference was observed in ischemic risk area between these groups.

As shown in FIG. 4, the following data of myocardial infarct size were obtained: control group: 24.3±2.4%, empty liposome group: 21.2±3.5%, adenosine-only group: 25.2±1.9%, adenosine-retaining liposome group (injection before ischemia): 11.6±2.5%, and adenosine-retaining liposome group (injection before reperfusion): 11.4±3.1%. Thus, infarct size was significantly reduced by adenosine-retaining liposomes in both the cases of injection before ischemia and injection before reperfusion.

Test Example 3

Ischemia-Reperfusion Test (Dog)

1. Ventricular Fibrillation Reduction Test

1) Test method

Adult beagle dogs (body weight: 8 to 12 kg, supplied by Oriental Yeast Co., Ltd.) were employed. Each of the dogs was anesthetized with pentobarbital sodium (30 mg/kg, intravenous injection) and then fixed in the dorsal position. A tube was inserted into the trachea, and artificial ventilation was carried out by means of a ventilator for animals. Thereafter, the carotid artery was exposed; thoracotomy was carried out at the thoracic sidewall; the left anterior descending coronary artery (LAD) was exposed; and a cannula was inserted into both the blood vessels, to thereby form a bypass between the carotid artery and the LAD. The bypass was occluded and released, to thereby prepare an ischemia-reperfusion model. The dog was subjected to 90 minutes of ischemia and 360 minutes of reperfusion. A drug sample was injected through a catheter indwelled in the jugular vein. During the test, arrhythmia was monitored through electrocardiography, and blood pressure was monitored by arterial blood pressure measurement. In addition, collateral blood flow was measured through the microsphere method.

Injection was initiated 10 minutes before reperfusion and continued for 120 minutes. The test was carried out in the following groups: 1) control group (empty liposomes, 12 mL/hour, n=7); 2) adenosine-retaining liposome group (12 mL/hour (30 μg/kg/minute), n=7); and 3) adenosine-retaining liposome group (36 mL/hour (300 μg/kg/minute), n=5) (adenosine concentration: 1.5 mg/mL for the adenosine-retaining liposome group 2) or 5 mg/mL for the adenosine-retaining liposome group 3)).

2) Test Results

In the control group, four of the seven dogs developed ventricular fibrillation during reperfusion. Meanwhile, in the adenosine-retaining liposome group 2), two of the seven dogs developed ventricular fibrillation during reperfusion, and in the adenosine-retaining liposome group 3), one of the six dogs developed ventricular fibrillation during reperfusion.

These data indicate that the adenosine-retaining liposomes of the present invention reduce ventricular fibrillation during reperfusion.

2. Myocardial Infarct Size Reduction Test

1) Test Method

The test was carried out in a manner similar to that of the ventricular fibrillation reduction test, and myocardial infarct size was measured as described below, to thereby determine the effect of the adenosine-retaining liposomes of the present invention in reducing myocardial infarct size.

2) Method for Measuring Myocardial Infarct Size

Each of the dogs was anesthetized 360 minutes after reperfusion, and then the heart was extirpated. A 2% Evans blue solution was injected into the circumflex artery and the right coronary artery to thereby stain a non-ischemic portion, and then the left ventricle was divided in five specimens in a minor axis direction. Thereafter, infarct size was calculated in a manner similar to that described in Test Example 2

3) Test Results

Figure 5:
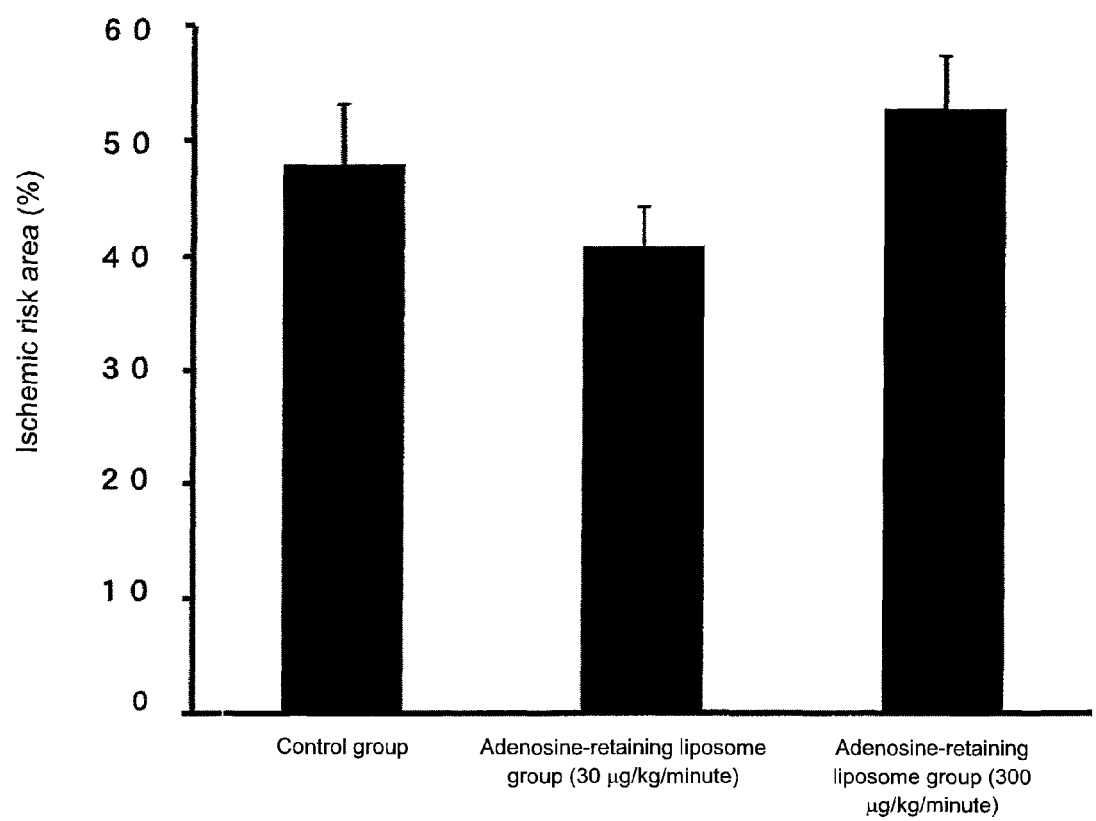
FIG. 5 is a graph showing the effect of a drug on ischemic risk area upon administration of the drug to an ischemia-reperfusion model dog.
Figure 6:
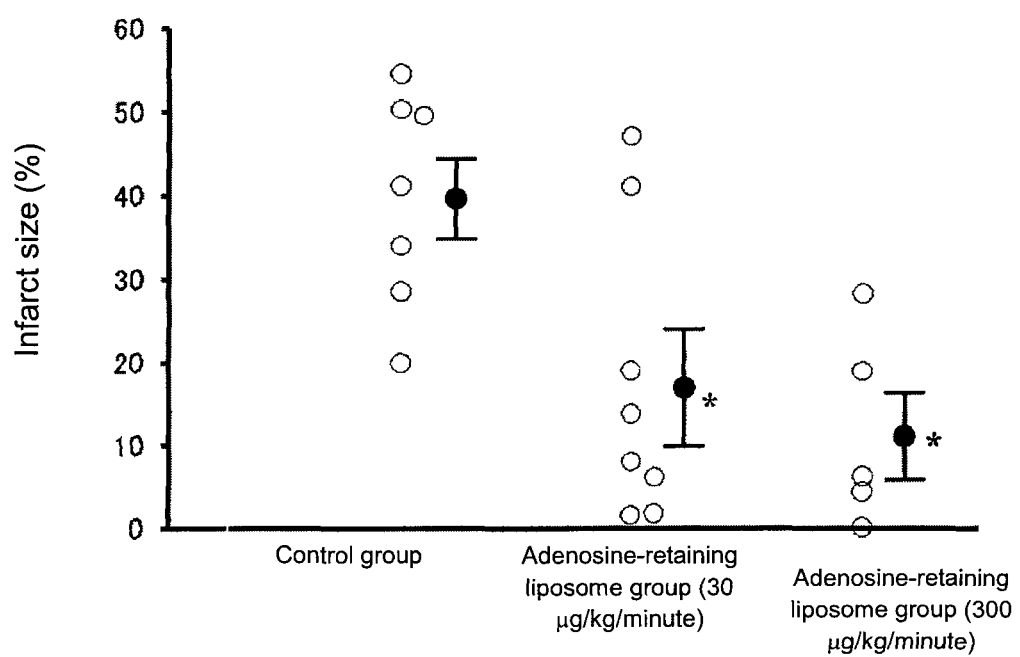
FIG. 6 is a graph showing the effect of a drug on infarct size upon administration of the drug to an ischemia-reperfusion model dog.

The results are shown in FIGS. 5 and 6. As shown in FIG. 5, the following data of ischemic risk area were obtained: control group: 48±5%, adenosine-retaining liposome group 2): 41±4%, and adenosine-retaining liposome group 3): 52±5%. Thus, no significant difference was observed in ischemic risk area between these groups. Also, no significant difference was observed in collateral blood flow between these groups.

As shown in FIG. 6, the following data of myocardial infarct size were obtained: control group: 40±5%, adenosine-retaining liposome group 2): 17±7%, and adenosine-retaining liposome group 3): 12±6%. These data indicate that the adenosine-retaining liposomes of the present invention significantly reduce infarct size.

The invention claimed is:

1. A method for treatment of myocardial ischemia-reperfusion injury without an increase in collateral blood flow, the method comprising administering an active agent consisting of a lipid membrane structure retaining adenosine to a subject in need thereof,
wherein said administering is intravenously,
wherein the lipid membrane structure contains (i) a phospholipid, (ii) a cholesterol and/or a cholestanol, and (iii) a polyethylene glycol derivative selected from the group consisting of
N-{carbonyl-methoxypolyethylene glycol-2000}-1,2-dipalmitoyl-sn-glycero-3-phosphoethanolamine,
N-{carbonyl-methoxypolyethylene glycol-5000}-1,2-dipalmitoyl-sn-glycero-3-phosphoethanolamine,
N-{carbonyl-methoxy-polyethylene glycol-750}-1,2-distearoyl-sn-glycero-3-phosphoethanolamine,
N-{carbonyl-methoxy-polyethylene glycol-2000}-1,2-distearoyl-sn-glycero-3-phosphoethanolamine, and
N-{carbonyl-methoxy-polyethylene glycol-5000}-1,2-distearoyl-sn-glycero-3-phosphoethanolamine as components thereof,
wherein the lipid membrane structure is a liposome,
wherein the ratio by mole of adenosine to the total lipid content of the phospholipid and cholesterol contained in the lipid membrane structure is ranges from 0.01 to 2,
wherein adenosine is administered in an amount effective to reduce the incidence of myocardial ischemia-reperfusion injury, said amount ranging from 2.25 mg/kg to 36 mg/kg, and
wherein a therapeutic benefit is observed after a single dosage.

2. The method according to claim 1, wherein the phospholipid is hydrogenated soybean lecithin.

3. The method according to claim 1, wherein the polyethylene glycol derivative is N-(carbonyl-methoxy-polyethylene glycol-2000}-1,2-distearoyl-sn-glycero-3-phosphoethanolamine.

4. The method according to claim 1, wherein the polyethylene glycol derivative is N-{carbonyl-methoxypolyethylene glycol-2000}-1,2-dipalmitoyl-sn-glycero-3-phosphoethanolamine.

5. The method according to claim 1, wherein the polyethylene glycol derivative is N-{carbonyl-methoxypolyethylene glycol-5000}-1,2-dipalmitoyl-sn-glycero-3-phosphoethanolamine.

6. The method according to claim 1, wherein the polyethylene glycol derivative is N-{carbonyl-methoxy-polyethylene glycol-750}-1,2-distearoyl-sn-glycero-3-phosphoethanolamine.

7. The method according to claim 1, wherein the polyethylene glycol derivative is N-{carbonyl-methoxy-polyethylene glycol-5000}-1,2-distearoyl-sn-glycero-3-phosphoethanolamine as components thereof.

8. The method according to claim 1, wherein said liposome is a single-membrane liposome.

9. The method according to claim 1, wherein said liposome is a multi-layer liposome.

10. The method according to claim 1, wherein said liposome has a particle size ranging from 50 nm to 5 μm.

11. The method according to claim 1, wherein said liposome has a particle size ranging from 50 nm to 200 nm.

12. The method according to claim 1, wherein adenosine is administered at a rate of 900 μg/kg/min or less.

13. The method according to claim 1, wherein the phospholipid is at least one species selected from the group consisting of phosphatidylethanolamine, phosphatidylcholine, phosphatidylserine, phosphatidylinositol, phosphatidylglycerol, cardiolipin, sphingomyelin, plasmalogen, and phosphatidic acid.

14. The method according to claim 1, wherein the liposome comprises phosphatidylcholine, cholesterol, and N-{carbonyl-methoxy-polyethylene glycol-2000}-1,2-distearoyl-sn-glycero-3-phosphoethanolamine.

15. The method according to claim 1, wherein the liposome retaining adenosine, adenosine is present in a lipid membrane of the liposome, inside of the liposome, or in a lipid layer of the liposome.

16. The method according to claim 1, wherein the drug is administered intravenously in an adenosine amount of 30 μg/kg/min to 900 μg/kg/min.

17. The method according to claim 1, wherein the drug is administered intravenously in an adenosine amount of 225 μg/kg/min to 900 μg/kg/min.

* * * * *